(12) United States Patent
Lee et al.

(10) Patent No.: US 8,747,925 B2
(45) Date of Patent: Jun. 10, 2014

(54) PHARMACEUTICAL COMPOSITION FOR TREATING DIABETES

(75) Inventors: Chen-Chia Lee, Taipei (CN); Wen-Hwa Chen, Taipei (TW); Tsung-Shann Jiang, Taipei (TW); Yu-Ju Lai, Taipei (TW); Shih-Jen Wang, Jghonghe (CN)

(73) Assignee: Phytohealth Corporation, Taipei (TW)

( * ) Notice: Subject to any disclaimer, the term of this patent is extended or adjusted under 35 U.S.C. 154(b) by 12 days.

(21) Appl. No.: 13/000,916

(22) PCT Filed: Jun. 22, 2009

(86) PCT No.: PCT/CN2009/000693
§ 371 (c)(1),
(2), (4) Date: Mar. 14, 2012

(87) PCT Pub. No.: WO2010/148533
PCT Pub. Date: Dec. 29, 2010

(65) Prior Publication Data
US 2012/0321731 A1    Dec. 20, 2012

(51) Int. Cl.
*A61K 36/00* (2006.01)
(52) U.S. Cl.
USPC ............................................. 424/773
(58) Field of Classification Search
None
See application file for complete search history.

(56) References Cited

U.S. PATENT DOCUMENTS

2004/0241253 A1 * 12/2004 Ikeda et al. .................. 424/725

FOREIGN PATENT DOCUMENTS

| CN | 1107737 A | * | 9/1995 |
| CN | 1116543 A | * | 2/1996 |
| JP | 62077329 A | * | 4/1987 |
| KR | 2006078123 A | * | 7/2006 |

OTHER PUBLICATIONS

"Cassia cinnamon". Retrieved from the Internet on: Dec. 11, 2013. Retrieved from the Internet: <URL: http://www.rxlist.com/cassia_cinnamon/supplements.htm>.*
"Ramulus cinnamomi (Cassia Cinnamon)". Retrieved from the Internet on: Dec. 22, 2013. Retrieved from the Internet: <URL: http://www.webmd.com/vitamins-supplements/ingredientmono-1002-Ramulus%20Cinnamomi%20(CASSIA%20CINNAMON). aspx?activeIngredientId=1002&activeIngredientName=Ramulus%20Cinnamomi%20(CASSIA%20CINNAMON)>.*
Yang, Jie, World Clinical Drugs, vol. 29, No. 2, 2008, pp. 94-100.

* cited by examiner

*Primary Examiner* — Amy L Clark
(74) *Attorney, Agent, or Firm* — Wolf, Greenfield & Sacks, P.C.

(57) ABSTRACT

The present invention provides a pharmaceutical composition for treating diabetes comprising Ramulus Cinnamomi, Radix et Rhizoma Rhei, Semen Persicae, Radix Rhizoma Glycyrrhizae, and *Cordyceps*. The use of the composition for the manufacture of a medicament for treating type II diabetes is also provided.

16 Claims, No Drawings

PHARMACEUTICAL COMPOSITION FOR TREATING DIABETES

RELATED APPLICATIONS

This application is a national stage filing under 35 U.S.C. §371 of International Application No. PCT/CN2009/000693, filed Jun. 22, 2009 and entitled "Pharmaceutical Composition For Treating Diabetes." The entire teachings and contents of this referenced application are incorporated by reference herein.

BACKGROUND OF THE INVENTION

In these years, the incidence of diabetes in the world is in rapid upward trend, wherein type II diabetes takes the largest of proportion. There is no certain conclusion on the pathology of type II diabetes. However, "insulin resistance" is one of the main characteristics. It now concludes that type II diabetes is related to the generic defect, anti-insulin receptor antibody, and hormones. Recently, it links the obesity and type II diabetes (Chapman M J., *Diab Vasc Dis Res,* 2009, Suppl 3:5-8). The general treatments for type II diabetes are dietary management, exercises, and oral administration of insulin and drugs for blood sugar control. However, the low insulin sensitivity limits the effects of drugs for decreasing blood sugar level and stimulating insulin secretion. Thus, it is important to study type II diabetes and insulin sensitivity.

At the present day, few oral medications or insulin sensitizer are applied, and most of which perform dissatisfied clinical treatment. Moreover, long term administration of insulin sensitizer may lead to pancreas failure and other possible side effects, i.e. heart failure, toxicity on liver cells and extraordinary medical expense as well. Therefore, to develop insulin sensitizer with low side effects is important and highly demanded.

BRIEF SUMMARY OF THE INVENTION

The present invention provides a pharmaceutical composition for treating type II diabetes comprising Ramulus Cinnamomi, Radix et Rhizoma Rhei, Semen Persicae, Radix Rhizoma Glycyrrhizae, and *Cordyceps*. According to one of the embodiment, the pharmaceutical can further comprise pharmaceutically acceptable carrier if necessary. The pharmaceutical composition of the present invention can improve the insulin sensitivity and treat diabetes, especially type II diabetes.

The present invention also provides use of a pharmaceutical composition for the manufacture of a medicament for treating diabetes, wherein the pharmaceutical composition comprises Ramulus Cinnamomi, Radix et Rhizoma Rhei, Semen Persicae, Radix Rhizoma Glycyrrhizae, and *Cordyceps*.

The details of one or more embodiments of the invention are set forth in the description below. Other features or advantages of the present invention will be apparent from the following tables and detailed description of several embodiments, and also from the appending claims.

DETAILED DESCRIPTION OF THE INVENTION

The present invention discovered a composition of Chinese herbs which is capable of improving insulin sensitivity without the side effects of clinical insulin sensitizers.

In one aspect, the present invention provides a pharmaceutical composition for treating type II diabetes comprising Ramulus Cinnamomi, Radix et Rhizoma Rhei, Semen Persicae, Radix Rhizoma Glycyrrhizae, and *Cordyceps*, and further comprising pharmaceutically acceptable carrier. According to the invention, the pharmaceutical composition comprises 15-25% Ramulus Cinnamomi, 30-40% Radix et Rhizoma Rhei, 15-25% Semen Persicae, 15-25% Radix Rhizoma Glycyrrhiza and 5-10% *Cordyceps*. According to one of the embodiment of the invention, the pharmaceutical composition comprises 20% Ramulus Cinnamomi, 35% Radix et Rhizoma Rhei, 20% Semen Persicae, 20% Radix Rhizoma Glycyrrhiza and 5% *Cordyceps*.

The term "diabetes" as used herein refers to type I diabetes, type II diabetes, or non-insulin dependent diabetes mellitus. According to the embodiment, the pharmaceutical composition of the present invention can be used for treating type II diabetes.

The term "insulin sensitivity" as used herein refers to in any forms of increasing the binding of insulin and its receptor and decreasing blood sugar, blood cholesterol, glycated albumin and glucagon, i.e. increasing the amounts of insulin receptors, or stimulating GLUT4 (Glucose transporter type 4) gene expression.

The term "treating" or "treatment" as used herein refers to administering the pharmaceutical composition of the invention to a subject that has type I or type II diabetes, or has a symptom of diabetes, or has a predisposition toward either diseases, with the purpose to ameliorate the resistant to insulin, reduce the glucose, triglyceride, cholesterol level in the blood, improve the expression of GLUT-4 gene, and increase the number of insulin receptors and beta-cells in pancreas, as shown in the embodiments.

According to one embodiment of the invention, the symptoms of polyuria (frequent urination), polydipsia (increased thirst) and polyphagia (increased hunger) of diabetes rats administered the pharmaceutical composition of the present invention are significantly ameliorated. According to another embodiment of the invention, the levels of blood sugar, triglyceride, total cholesterol and glycated albumin in the serum of the rats administered the pharmaceutical composition of the invention decrease and maintain at normal condition.

Ramulus Cinnamomi used in the pharmaceutical composition of the present invention, also named as "Gui Zhi", is prepared from the dried branches and twigs of the Cinnamomum Cassia Presl plant. Traditionally, Gui Zhi is used for urinary tract disorders, mucous membrane inflammation, syphilis, cold, and as a tonic and "blood purifier".

Radix et Rhizoma Rhei used in the pharmaceutical composition of the present invention, also named as "Da Huang". Da Huang is often used for constipation, diarrhea, dyspepsia, gastritis, virus hepatitis, pancreatic infection, bowel movement relief when anal fissures are present, and hemorrhoids. According to the invention, Da Huang is prepared from the dried rhizome of the plants. *Rheum palmatum L., Rheum tanguticum Maxim.* ex BLF, or *Rheum officinale Baill.*

Semen Persicae used in the pharmaceutical composition of the present invention, also named as "Tao Ren", is prepared from the dried peach kernel of *Prunus persica* (L.) Batsch or *Prunus davidiana* (Can.) France. Usually, Tao Ren is used for anti coagulation, anti hypertensive, inhibits pain, anti inflammation, detoxification, anti-allergenics, and promoting bowel movements.

Radix Rhizoma Glycyrrhiza used in the pharmaceutical composition of the present invention, also named as "licorice", is the dried rhizome of the plant and has lots of usages. In traditional Chinese medicine, licorice is used for relief of the pain, flavor, cough suppression. In the prescription, it often used as an adjuvant. In the recent study, the active components of licorice includes glycyrrhizin, glycyrrhizic acid and liquoricone, and has the pharmaceutical effects on detoxification, anti-inflammation, anti-virus, anti-bacterial, anti-canter, anti-oxidant, liver protection and anti-ulcer. According to the invention, Radix Rhizoma Glycyrrhiza is inner Mongo origin.

Cordyceps, or Cordyceps sinensis, is also called the "caterpillar fungus." In the wild it grows on and acquires nutrients from several species of caterpillars. In China, it is referred to as "winter worm, summer grass." In traditional Chinese medicine, C. sinensis is considered to benefit the lung and kidney, and has the pharmaceutical effects on cough, night sweats, homeostasis, and removing phlegm. For the last several decades, some active ingredients of Cordyceps had been found and extracted, including cordycepin (3'-deoxyadenosine) and Cordyceps Sinensis polysaccharide. These compounds are also confirmed to have the effects of anti-bacterial, anti-cancer, pesticide, and immunity regulation.

"Cordyceps" in the composition of the present invention can be prepared from nature Cordyceps sinensis, cultural Cordyceps, i.e. Hirsutella sinensis, Acremonium terricola, Cordyceps Sp. Mycelia, and Paecilomyces cicadae (Miquel.) Samson, or extracted active ingredients, including cordycepin (3'-deoxyadenosine) and Cordyceps Sinensis polysaccharide.

The pharmaceutical composition of the present invention can be prepared by general method, and further comprise one or more pharmaceutically acceptable carrier. The term "pharmaceutically acceptable carrier" used herein encompasses any of the standard pharmaceutical carriers. Such carriers may include, but are not limited to: saline, buffered saline, dextrose, water, glycerol, ethanol and combinations thereof.

The pharmaceutical composition of the present invention may be constituted into any form suitable for orally administration. For example, compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In addition to standard carriers, an oral pharmaceutical composition of the present invention may be supplemented with one or more excipients that are normally employed in oral formulations, such as surfactants, solubilizers, stabilizers, emulsifiers, thickeners, coloring agents, sweetening agents, flavoring agents, and preservatives. Such excipients are well known to those skilled in the art.

In another aspect, the present invention provides use of a pharmaceutical composition for the manufacture of a medicament for treating diabetes, wherein the pharmaceutical composition comprises Ramulus Cinnamomi, Radix et Rhizoma Rhei, Semen Persicae, Radix Rhizoma Glycyrrhizae, and Cordyceps.

The term "an effective amount" as used herein refers to the amount of the pharmaceutical composition that is required to confer the intended therapeutic effect in the subject. Effective amounts may vary, as recognized by those skilled in the art, depending on the psychological condition of the subject in need (i.e. weight, disease, or gender), excipient usage, and the possibility of co-usage with other agents based on the disclosure in the specification. For example, the dosage used in human is close to the middle dose of the claimed composition. After dose conversion, an adult is suggested to take 2 g a dose, three times per day.

The pharmaceutical composition of the present invention can be used along with any clinical drugs for treating diabetes, as an adjuvant. The pharmaceutical composition effectively improves the insulin sensitivity so as to lower the dosage of clinical drugs and decrease the side effects accompanying the drugs.

The invention will now be described more specifically with reference to the following specific examples relating to particular, presently preferred embodiments. It should be noted that the following descriptions of preferred embodiments of this invention are presented herein for the purpose of illustration and description only; they are not intended to be exhaustive or to be limited to the precise form disclosed.

EXAMPLE 1

Establishment of Diabetes Rat Model and Grouping

SPF SD (Sprague-Dawley) male rats were purchased by Animal Research Center, Guangzhou University of Chinese Medicine in China. The cultivated condition was under light and night 12 hours each, temperature at 23±2° C., and humidity between 40-78%. All animals were free to eat and drink. After 1 week, the rats were randomly grouped into normal group, control group, comparison group (fed with partial components of the pharmaceutical composition, including (1) Cordyceps alone; (2) Radix et Rhizoma Rhei alone; (3) Ramulus Cinnamomi and Semen Persicae; and (4) Radix et Rhizoma Rhei, Ramulus Cinnamomi, Semen Persicae, and Radix Rhizoma Glycyrrhiza), and experimental group (fed with the pharmaceutical composition containing 20% Ramulus Cinnamomi (Gui Zhi), 35% Radix et Rhizoma Rhei (Da Huang), 20% Semen Persicae (Tao Ren), 20% Radix Rhizoma Glycyrrhiza (licorice) and 5% Cordyceps at low, middle, and high dosage).

The rats of the normal group were fed with ordinary chow, and the control group was fed with high-fat/high-sucrose diet (15% sucrose, 4% cholesterol, 0.3% bile salt, 10% lard, 10% york, 61% ordinary chow). After 8 weeks, the rats were injected intraperitoneally with 30 mg/kg streptozotocin (STZ, Sigma Corporation, USA). Three days after the injection, Accu-check Advantage Blood Glucose Testing System (Roche Corporate) was used to choose diabetes rats having fasting glucose≥11 mmol/L.

Among these diabetes rats, according to the different feed by intragastric injection lasting 8 weeks, were randomly grouped into nine groups by body weight and blood glucose as below.

| Group | No. | Intragastric injection (per day/rat) |
| --- | --- | --- |
| Normal group (A) | 20 | None |
| Control group (B) | 20 | Distilled water |
| Comparison group-I (C) | 20 | 4 mg Cordyceps |
| Comparison group-II (D) | 20 | 29 mg Da Huang |
| Comparison group-III (E) | 20 | 16.5 mg Gui Zhi<br>16.5 mg Tao Ren |
| Comparison group-IV (F) | 20 | 29 mg Da Huang<br>16.5 mg Tao Ren<br>16.5 mg Gui Zhi<br>16.5 mg licorice |
| Low dose group (G) | 20 | 14.5 mg Da Huang<br>8.25 mg Tao Ren<br>8.25 mg Gui Zhi<br>8.25 mg licorice<br>2 mg Cordyceps |
| Middle dose group (H) | 20 | 29 mg Da Huang<br>16.5 mg Tao Ren<br>16.5 mg Gui Zhi |

-continued

| Group | No. | Intragastric injection (per day/rat) |
|---|---|---|
| High dose group (I) | 20 | 16.5 mg licorice<br>4 mg Cordyceps<br>58 mg Da Huang<br>33 mg Tao Ren<br>33 mg Gui Zhi<br>33 mg licorice<br>8 mg Cordyceps |
| Biguanides group (J) | 20 | 14 mg Biguanides |

The ingredients for intragastric injection were grinded into powder and dissolve in distilled water according to the above proportion. The rats in each group were administered once per day for 8 weeks.

EXAMPLE 2

Determination of the Effectness on Ameliorating the Symptoms of Diabetes

After 8 weeks of administration, 10 rats were chosen randomly in each group, recorded the performance on food intake, drinking, urine volume; and glucose tolerance test on these rats was carried out. The amounts of insulin, glucagons, glycated albumin and blood cholesterol in the blood were also measured.

Physiological State

The classic symptoms of diabetes are polyuria, polydipsia, polyphagia, and weight loss. The changes on physiological state of experimental rats at Week 0 (before treatment) and Week 8 (after treatment) were recorded and the results were shown in Table I and Table II.

Before the treatment, the drinking, urine volume, and food intake of the control group, comparison group and experimental group were similar with normal group ($p>0.05$); however, the food intake increased from day to day ($p<0.01$). At Week 8, drinking, urine volume, and food intake of the control group increased as compared to normal rats ($p<0.01$), but the body weight of the control group was lighter than that of normal group ($p<0.01$). Among the treatment groups, all rats had less food intake, drinking and urine volume, but heavier body weight as compared with control rats ($p<0.01$). Drinking, urine volume, and food intake of most rats in all comparison groups increased compared with middle dose group; however, the body weight decreased ($p<0.01$). Drinking and urine volume of low dose, high dose and biguanides group were similar compared with middle dose group ($p>0.05$); however, food intake increased and body weight decreased ($p<0.01$ or $p<0.05$). After treatment, middle dosage of the pharmaceutical composition exhibited the same effeteness on ameliorating the classic symptoms of diabetes.

TABLE I

Drinking and Urine Volume of Diabetes Rats at Week 0 and Week 8

| Group | n | Drinking (ml/day) | | Urine volume (ml/day) | |
|---|---|---|---|---|---|
| | | 0 week | 8 weeks | 0 week | 8 weeks |
| A | 10 | 30.57 ± 8.67 | 65.35 ± 12.62 | 16.31 ± 5.64 | 33.46 ± 8.86 |
| B | 9 | 35.64 ± 7.83 | 85.23 ± 10.85# | 16.84 ± 5.26 | 55.67 ± 9.19# |
| C | 10 | 37.61 ± 7.57 | 68.18 ± 11.34#Δ▲ | 17.62 ± 4.19 | 38.37 ± 8.26#Δ▲ |
| D | 9 | 35.37 ± 6.08 | 66.12 ± 10.41#Δ | 15.17 ± 4.09 | 40.21 ± 10.37#Δ▲ |
| E | 10 | 34.68 ± 5.92 | 72.38 ± 8.19#Δ▲ | 17.94 ± 4.51 | 39.34 ± 9.68#Δ▲ |
| F | 9 | 35.33 ± 8.31 | 68.67 ± 11.49#Δ▲ | 16.21 ± 4.53 | 40.37 ± 10.18#Δ▲ |
| G | 10 | 35.97 ± 9.02 | 65.67 ± 12.95#Δ | 15.03 ± 5.07 | 35.07 ± 8.34#Δ |
| H | 10 | 36.89 ± 7.39 | 63.68 ± 13.02#Δ | 17.34 ± 4.95 | 33.64 ± 9.07#Δ |
| I | 9 | 34.51 ± 8.62 | 66.54 ± 11.18#Δ | 15.62 ± 6.25 | 35.45 ± 10.32#Δ |
| J | 9 | 37.91 ± 7.61 | 65.54 ± 10.63#Δ | 16.06 ± 4.91 | 33.07 ± 8.38#Δ | indicates statistical significance compared with the normal group ($p < 0.01$).
Δindicates statistical significance compared with the normal group ($p < 0.01$).
▲indicates statistical significance compared with middle dose group ($p < 0.01$).

TABLE II

Drinking and Urine Volume of Diabetes Rats at Week 0 and Week 8

| Group | n | Drinking (ml/day) | | Urine volume (ml/day) | |
|---|---|---|---|---|---|
| | | 0 week | 8 weeks | 0 week | 8 weeks |
| A | 10 | 18.57 ± 6.67 | 55.35 ± 12.62 | 128.34 ± 8.01 | 433.24 ± 35.67 |
| B | 9 | 23.64 ± 7.83 | 85.23 ± 10.85# | 126.84 ± 39.46 | 358.67 ± 27.19# |
| C | 10 | 25.64 ± 6.57 | 68.18 ± 11.34#Δ▲ | 128.62 ± 7.19 | 398.37 ± 32.26#Δ▲ |
| D | 9 | 24.37 ± 8.08 | 76.12 ± 10.41#Δ▲ | 124.17 ± 8.09 | 385.21 ± 29.37#Δ▲ |
| E | 10 | 22.68 ± 6.92 | 72.38 ± 10.19#Δ▲ | 127.94 ± 9.51 | 380.34 ± 25.68#Δ▲ |
| F | 9 | 25.33 ± 7.31 | 68.67 ± 11.49#Δ▲ | 129.21 ± 8.53 | 370.37 ± 28.18#Δ▲ |
| G | 10 | 24.97 ± 8.02 | 65.67 ± 12.95#Δ▲▲ | 126.03 ± 9.07 | 405.07 ± 30.34#Δ▲ |
| H | 10 | 23.89 ± 7.39 | 61.68 ± 13.02#Δ | 128.34 ± 7.95 | 420.64 ± 29.07#Δ |
| I | 9 | 24.51 ± 8.62 | 66.54 ± 11.18#Δ▲ | 125.62 ± 8.25 | 386.06 ± 26.32#Δ▲ |
| J | 9 | 24.91 ± 8.61 | 63.54 ± 10.63#Δ | 129.06 ± 8.91 | 418.07 ± 27.38#Δ | indicates statistical significance compared with the normal group ($p < 0.01$).
Δindicates statistical significance compared with the normal group ($p < 0.01$).
▲indicates statistical significance compared with middle dose group ($p < 0.01$).
▲▲indicates statistical significance compared with middle dose group ($p < 0.05$).

Glucose Tolerance Test

The glucose concentration in human blood shall maintain in a constant range, which is so-called "fasting plasma glucose (FPG)", and will arise after the meal, which is so-called "post-prandial blood glucose (PBG)". The concentration of blood glucose will get back to normal level within one or two hours after the meal due to the function of insulin. Diabetes patients are considered to have impaired glucose tolerance because of the lack of insulin or insulin resistance.

A glucose tolerance test in medical practice is the administration of glucose to determine how quickly it is cleared from the blood. Before collecting the blood from retro-orbital plexus, the rats fasted for 8 hours and then received 2 g/kg glucose intraperitoneally. The blood glucose level was measured before the meal (FBG, fasting blood glucose) or post-prandial (1 h-PBG or 2 h-PBG). The results were shown in Table III.

The FBG, 1 h-PBG, and 2 h-PBG of control rats were all significantly higher than those of normal rats ($p<0.01$). As compared with control group, the FBG, 1 h-PBG, and 2 h-PBG of rats in each comparison group, different dose group and biguanides group were significantly lower than control group ($p<0.01$). As compared with each comparison group, the FBG and 2 h-PBG of middle and high dose group were significantly decreased ($p<0.01$). As compared with biguanides group, the middle and high group were equally efficacious for decreasing FBG and 2 h-PBG.

TABLE III

The Results on Glucose Tolerance Test for Each Group

| Group | n | FBG (mmol/L) | 1 h-PBG (mmol/L) | 2 h-PBG (mmol/L) |
|---|---|---|---|---|
| A | 10 | 4.85 ± 0.65 | 8.56 ± 1.07 | 4.68 ± 0.57 |
| B | 9 | 11.90 ± 1.06 | 16.84 ± 3.57 | 16.59 ± 3.06 |
| C | 10 | 8.65 ± 0.84# | 11.57 ± 2.34# | 10.18 ± 2.67# |
| D | 9 | 9.38 ± 0.73# | 11.34 ± 1.98# | 10.34 ± 1.67# |
| E | 10 | 9.24 ± 0.67# | 12.86 ± 2.67# | 10.23 ± 1.94# |
| F | 9 | 9.74 ± 0.84# | 11.29 ± 1.61# | 10.08 ± 1.62# |
| g | 10 | 8.09 ± 0.64# | 10.23 ± 1.28# | 10.64 ± 1.61# |
| h | 10 | 6.59 ± 0.57#△▲ | 9.34 ± 2.35# | 8.01 ± 1.17#△▲ |
| I | 9 | 6.84 ± 0.76#△▲ | 10.06 ± 1.54# | 8.43 ± 1.08#△▲ |
| J | 9 | 6.48 ± 0.49#△▲ | 9.75 ± 2.64# | 7.59 ± 1.26#△▲ | indicates statistical significance compared with the control group ($p < 0.01$).
△indicates statistical significance compared with the comparison groups ($p < 0.01$).
▲indicates statistical significance compared with the low dose group ($p < 0.01$).

Measurement of the Level of Serum Albumin, Blood Cholesterol, Insulin, Glucagon and Detection of Insulin Sensitivity Index Blood of all experimental rats was collected from abdominal aorta and used for measuring triglyceride by GPO-PAP method (Quan Guo Lin Chuang Jian Cao Zuo Shou Ce, 1997, $2^{nd}$ edition: 275), and total cholesterol by CHOP-PAP method (Zhong Hua Yi Xue Jian Yan Za Zhi, 1995, 18(3): 183-186).

The serum was separated from the collected blood, and further used for detection of insulin and glucagon by a radio immunoassay kit, which was provided by China Institute of Atomic Energy. Meanwhile, the serum was also used for detection of glycated albumin by fructosamine test.

Insulin sensitivity index (ISI) was calculated by the formula published by Li, Guang-Wei et al (Zhong Hua Nei Ke Za Zhi, 1993, 32(10):656-660), which is the inverse of the sum of logarithmically expressed value of fasting insulin (FIns) and FBG: $[\ln(1/\text{Fins} \times \text{FBG})]$ All the testing results were listed on Table IV and V.

As shown in Table VI, glycated albumin, triglyceride and total cholesterol of the control group were all significantly higher that those of normal group ($p<0.01$). As compared with the control group, the glycated albumin, triglyceride and total cholesterol of all different dose groups and biguanides group were significantly lower that those of the control group ($p<0.01$ of $p<0.05$). As compared with each comparison group, glycated albumin and triglyceride of different dose groups and biguanides group significantly decreased ($p<0.01$). As compared with low dose group, middle dose group, high dose group and biguanides group significantly decreased the level of glycated albumin ($p<0.01$ of $p<0.05$), but had similar efficacy on decreasing triglyceride and total cholesterol.

TABLE IV

The Concentration of Glycated Albumin, Triglyceride and Total Cholesterol of the Rats Serum

| Group | n | Glycated albumin (mmol/L) | Triglyceride (mmol/L) | Total Cholesterol (mmol/L) |
|---|---|---|---|---|
| A | 10 | 1.85 ± 0.54 | 0.82 ± 0.30 | 1.84 ± 0.17 |
| B | 9 | 3.67 ± 1.23 | 2.56 ± 0.49 | 2.48 ± 0.31 |
| C | 10 | 2.34 ± 0.62# | 1.54 ± 0.37# | 2.21 ± 0.27 |
| D | 10 | 2.43 ± 0.71## | 1.84 ± 0.51## | 1.94 ± 0.37 |
| E | 10 | 2.93 ± 0.51 | 1.51 ± 0.67# | 2.13 ± 0.28 |
| F | 9 | 2.64 ± 0.69## | 1.43 ± 0.53# | 2.04 ± 0.39 |
| G | 10 | 1.98 ± 0.68# | 0.97 ± 0.41# | 1.74 ± 0.26# |
| H | 10 | 1.27 ± 0.44#△▲▲ | 0.86 ± 0.48#△ | 1.62 ± 0.31# |
| I | 9 | 1.23 ± 0.34#△▲▲ | 0.97 ± 0.53#△ | 1.79 ± 0.23## |
| J | 9 | 1.14 ± 0.38#△▲▲ | 0.72 ± 0.51#△ | 1.53 ± 0.38# | indicates statistical significance compared with the control group ($p < 0.01$).
indicates statistical significance compared with the control group ($p < 0.05$).
△indicates statistical significance compared with the comparison groups ($p < 0.01$).
▲indicates statistical significance compared with the low dose group ($p < 0.01$).
▲▲indicates statistical significance compared with the low dose group ($p < 0.05$).

As shown in Table V, fasting insulin and glucagon of the control group were significantly higher than the normal group ($p<0.01$). As compared to the control group, fasting insulin and glucagon of most comparison groups, different dose groups and biguanides group significantly decreased ($p<0.01$). As compared to all comparison groups, fasting insulin and glucagon of middle dose group, high dose group and biguanides group significant decreased ($p<0.01$). As compared to the low dose group, fasting insulin and glucagon of middle dose group, high dose group and biguanides group significant decreased ($p<0.05$). Insulin sensitivity index of the control group was significantly lower than that of the normal group ($p<0.01$). Most comparison groups, different dose groups and biguanides group have significantly higher ISI compared with the control group ($p<0.01$ of $p<0.05$). As compared to each comparison group, insulin sensitivity index of each dose group and biguanides group significantly increased ($p<0.01$).

TABLE V

The Concentrations of Glycated Albumin, Triglyceride and Total Cholesterol of the Rats Serum

| Group | N | Insulin (uIU/L) | Glucagons (ng/L) | ISI |
|---|---|---|---|---|
| A | 10 | 21.56 ± 3.72 | 272.6 ± 53.4 | −4.02 ± 0.24 |
| B | 9 | 34.31 ± 4.24 | 542.7 ± 82.7 | −5.56 ± 0.19 |
| C | 10 | 26.37 ± 2.64# | 384.4 ± 62.5# | −5.03 ± 0.32## |
| D | 10 | 25.84 ± 3.68# | 423.5 ± 54.1# | −5.24 ± 0.37 |
| E | 10 | 27.81 ± 3.27# | 469.1 ± 61.8# | −5.17 ± 0.28 |
| F | 9 | 26.34 ± 4.25# | 427.1 ± 51.7# | −5.01 ± 0.36## |
| G | 10 | 26.37 ± 3.29# | 405.4 ± 41.8# | −4.56 ± 0.39#△ |

TABLE V-continued

The Concentrations of Glycated Albumin, Triglyceride and Total Cholesterol of the Rats Serum

| Group | N | Insulin (uIU/L) | Glucagons (ng/L) | ISI |
|---|---|---|---|---|
| H | 10 | 23.29 ± 2.68#∆▲ | 310.3 ± 48.6#∆▲ | −4.37 ± 0.34#∆ |
| I | 9 | 22.31 ± 3.16#▲ | 291.8 ± 45.1#∆▲ | −4.33 ± 0.29#∆ |
| J | 9 | 20.38 ± 3.19#∆▲ | 302.4 ± 42.1#∆▲ | −4.25 ± 0.28#∆ | indicates statistical significance compared with the control group ($p < 0.01$).
indicates statistical significance compared with the control group ($p < 0.05$).
∆indicates statistical significance compared with each comparison group ($p < 0.01$).
▲indicates statistical significance compared with the low dose group ($p < 0.01$).

In view of the results from Tables I-V, the pharmaceutical composition of the present invention is capable of ameliorating the classic symptoms of the diabetes, and maintains the normal level of blood sugar. Moreover, the concentrations of other diabetes related signs, i.e. glycated albumin, glucagon and cholesterol were also significantly decreased. In summary, the middle and high dosage of the pharmaceutical composition of the invention had similar efficacy as compared to one of clinical drug, i.e. biguanides, and do not yield any adverse effects.

Incensement of insulin sensitivity is the main aim for treating diabetes. However, commercial insulin sensitizers are few, expensive and accompanied with lots of adverse effects, which can not satisfy the diabetes patients' needs. According to the results in Table V, the pharmaceutical composition of the invention significantly increased ISI as compared to other groups.

EXAMPLE 3

Quantitative Analysis of Insulin Receptor (InsR) on Liver Cell Membranes and Gene Expression of GluT4 mRNA In order to demonstrate the efficacy on increasing insulin sensitivity so as to treat diabetes, a second experiment was conducted. In this experiment, ten rats were randomly chosen as normal group, and setting up the same animal model as described in Example 1. Other rats were grouped randomly (20 rats/group) according to body weight and blood sugar as following table.

| Group | Intragastric injection (per day/rat) |
|---|---|
| Normal group | None |
| Control group | Distilled water |
| Middle dose group | 29 mg Da Huang |
| | 16.5 mg Tao Ren |
| | 16.5 mg Gui Zhi |
| | 16.5 mg licorice |
| | 4 mg Cordyceps |
| Biguanides group | 14 mg Biguanides |

The ingredients for intragastric injection were grinded into powder and dissolve in distilled and were administered to rats once a day for 8 weeks. At Week 8, the rats randomly chosen from each group was conducted the test for detecting insulin receptor on liver cells membrane and the gene expression of GLUT4.

Quantitative Analysis of Insulin Receptor (InsR) on Liver Cell Membranes

After 8 weeks fed with middle dose of the claimed composition, the rats were sacrificed, and the liver tissue was collected and minced. The grinded liver tissue was mixed with four times of volume of the buffer (1 mmol/L NaHCO3, 0.5 mmol/L CaCl2, pH7.5) at 8000 rpm. The mixed sample was added into five times of buffer to dilute, and then centrifuged with 800×g for 15 minutes followed filtrated by gauze. The supernatant was collected, and further centrifuged again with 27000×g for 20 minutes. The pellet was collected, and 7.5 ml sucrose (70 g/L (w/w)) was added to allow the final concentration to 48 g/L. The sample was loaded on the bottom of the microtube, and then loaded 9 ml of 45 g/L, 8 ml of 41 g/L, and 7 ml of 37 g/L of sucrose in the order named. The microtube was centrifuged at 78000×g for 3 hours, and then the interface between 37 g/L and 41 g/L sucrose was collected. The collection was diluted by 1 mmol/L NaHCO3 (pH 7.5), and then centrifuged for 20 minutes to collect the pellet. After an appropriate dilution, the concentration of membrane proteins was detected by Lowry method (Lowry Ohio, et al., *Bio Chem* 193(1):265-275, 1951).

The test was conducted on ice. Final concentration of 0, 0.015, 0.15, 1.5, 6 and 50 nmol/L non-labeled insulin was separately added into different tubes, and then each tube was further added 83.3 Bq iodine-labeled insulin (114-125 I-Ins) and 65 µg membrane proteins. The final reactive mixture was complemented by the reaction buffer (1 g/L BSA and 0.05 mmol/L Tris-HCl), and then was shaken for 20 hours at 4° C. The ligand-receptor complex was collected and washed by distilled water three times, then detected by a gamma counter (Pharmacia LKB, Sweden) to determine the radioactivity.

The radioactivity of standard Ins (at concentration of 50 nmol/L) was regarded as non-specific binding (NSB), and the subtraction between NSB and the radioactivity of sample (S) was regarded as specific binding (B); total radioactivity was labeled as T, and the subtraction between T and S was regarded as libratory $^{125}$I-Ins value (F).

SPSS 13.0 software is used for statistical analysis after obtaining the above data. The value of B/F was first calculated: B/F=(S−NSB)/(T−S). There are two kinds of insulin receptors: high affinity and low affinity. The two corresponding affinity constants (K1-high affinity, K2-low affinity) were minus inverse of asymptotic slope, and the x-intercept crossed with two asymptotes was the numbers of receptors that bound insulin (R1-high affinity, R2-low affinity).

Measurement of GLUT4 Gene Expression

GLUT4 is the insulin-regulated glucose transporter found in adipose tissues and striated muscle (skeletal and cardiac) that is responsible for insulin-regulated glucose disposal. When insulin binds its receptor, a serious signal pathway occurs and stimulating the expression of GLUT4. Therefore, the expression of GLUT4 is a negative correlation with insulin resistant.

When the rats treated for 8 weeks were sacrificed, the quadriceps was quickly separated from back limbs and then fixed into 4% formaldehyde for 4 hours. Next, the samples were embedded by wax and cut into 5 µm slices. The expression level of GLUT4 mRNA was determined by a GLUT4 mRNA in Situ Hybridization (ISH) kit (Wuhan Boster Biological Technology, Ltd.). The test was referred to the manual followed the kit.

As shown in Table VI, the numbers of insulin receptors of the control group was higher than that of the normal group ($p<0.01$); however, there was no significant difference on K1 and K2 compared to the normal group ($p>0.05$). As compared with the control group, the number of insulin receptor of the middle dose group was significant increased (p<0.01). As compared with the control group, the number of insulin receptor of the biguanides group was significant increased (p<0.01). As compared with the biguanides group, there was no significant difference on the numbers and affinity constant of insulin receptors of the middle dose group (p>0.05). The GLUT4 gene expression level of the control group was significant lower that that of the normal group (p<0.01). As compared with the control group, the GLUT4 gene expression level of the middle dose group and biguanides group significantly increased (p<0.01). There was no significant difference on the GLUT 4 gene expression level between the middle dose group and biguanides group (p>0.05).

In sum, the claimed composition is capable of increasing GLUT4 gene expression, and the number of the insulin receptors on liver cells membrane, which leads to enhance the insulin sensitivity and the metabolisms of glucose.

TABLE VI

The Effect of Biguanides and the Claimed Composition on Insulin Receptors and GLUT4 Gene Expression

| Group | Insulin Receptors on Liver Cell Membrane | | | | GLUT4 expression |
|---|---|---|---|---|---|
| | K1 mol/L ($\times 10^{-9}$) | K2 mol/L ($\times 10^{-8}$) | R1 mol/mg ($\times 10^{-12}$) | R2 mol/mg ($\times 10^{-12}$) | (Avg. light density) |
| Normal | 13.54 ± 4.78 | 14.68 ± 5.76 | 0.26 ± 0.13 | 3.35 ± 1.38 | 0.57 ± 0.04 |
| Control | 12.25 ± 3.62 | 13.04 ± 4.13 | 3.14 ± 1.27 | 5.11 ± 2.14 | 0.27 ± 0.02 |
| Biguanides | 13.24 ± 3.28 | 12.35 ± 5.02 | 5.57 ± 1.54# | 6.44 ± 2.38## | 0.49 ± 0.05# |
| Middle dose group | 13.45 ± 3.67 | 13.24 ± 4.95 | 6.24 ± 1.38# | 6.69 ± 2.13# | 0.46 ± 0.04# |

K1: affinity constant of high affinity insulin receptors
K2: affinity constant of low affinity insulin receptors
R1: the numbers of high affinity insulin receptors on the cell membrane
R2: the numbers of low affinity insulin receptors on the cell membrane
indicates statistical significance compared with the control group ($p < 0.01$).
indicates statistical significance compared with the control group ($p < 0.05$).

EXAMPLE 4

Observation of the Pathology of the Pancreas

In the second experiment, the rats were scarified after the treatment of middle dose of the claimed composition for 8 weeks, and then the appropriate size of the pancreas was collected. After fixed with 10% formaldehyde, the samples were cut into 5 μm, and then stained by hematoxylin and eosin. The slices were observed by microscope under 400× magnifications, and the numbers of beta-cells were counted and recorded as shown in Table VII.

The pancreas of the diabetes rats was paler and glutinous than normal rats observed with unaided eyes. When observed with the microscopy, it found that β-cells of the normal rats were round in shape and had abundant plasma, but those of diabetes rats were shrink and degenerative. It found that the island density of the middle dose group and biguanides group decreased, and the numbers of β-cells of both groups significantly increased compared with the control group (p<0.01). As compared to biguanides group, the number of β-cells of the middle dose group significantly increased (p<0.01).

It is known that β-cells of the diabetes patients may be damaged and degenerative along with the disease process so as to diminish insulin secretion. According to the above result, it demonstrates that the claimed composition has the efficacy on repairing the damaged β-cells and stimulating the insulin secretion, which can decrease the usage of the drugs for lowering blood sugar.

TABLE VII

The Effect on the Numbers of Beta-cells in Pancreas ($\bar{x} \pm S$)

| Group | n | Cells/Scope (400x) |
|---|---|---|
| Normal | 20 | 58.20 ± 15.30 |
| Control | 18 | 35.50 ± 13.51#▲ |
| Biguanides | 19 | 42.17 ± 12.06#Δ▲ |
| Middle dose group | 18 | 45.58 ± 15.06#Δ | indicates the significant difference compared with the normal group ($p < 0.01$).
Δindicates the significant difference compared with the control group ($p < 0.01$).
▲indicates the significant difference compared with the middle dose group ($p < 0.01$).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A pharmaceutical composition for treating diabetes comprising Ramulus Cinnamomi, Radix et Rhizoma Rhei, Semen Persicae, Radix Rhizoma Glycyrrhizae, and *Cordyceps*, wherein the pharmaceutical composition comprises the Ramulus Cinnamomi in an amount of 15-25%, the Radix et Rhizoma Rhei in an amount of 30-40%, the Semen Persicae in an amount of 15-25%, the Radix Rhizoma Glycyrrhiza in an amount of 15-25% and the *Cordyceps* in an amount of 5-10%.

2. The pharmaceutical composition of claim 1, wherein the pharmaceutical composition comprises 20% Ramulus Cinnamomi, 35% Radix et Rhizoma Rhei, 20% Semen Persicae, 20% Radix Rhizoma Glycyrrhiza and 5% *Cordyceps*.

3. The pharmaceutical composition of claim 1, wherein the pharmaceutical composition improves insulin sensitivity.

4. The pharmaceutical composition of claim 1, wherein the pharmaceutical composition facilitates insulin to bind its receptor.

5. The pharmaceutical composition of claim 1, wherein the pharmaceutical composition increases the absorption of glucose by skeleton muscle and adipocytes and effectively decreasing blood sugar concentration.

6. The pharmaceutical composition of claim 1, wherein the treatment of diabetes results from the improvement of insulin sensitivity.

7. The pharmaceutical composition of claim 1, wherein the diabetes is type II diabetes.

8. The pharmaceutical composition of claim 1 further comprising an excipient or a pharmaceutically acceptable carrier.

9. The pharmaceutical composition of claim 1, wherein the pharmaceutical composition is formulated for oral administration.

10. A method for treating diabetes, comprising administrating to a subject in need thereof a therapeutically effective amount of a pharmaceutical composition comprising Ramulus Cinnamomi, Radix et Rhizoma Rhei, Semen Persicae, Radix Rhizoma Glycyrrhizae, and *Cordyceps*, wherein the pharmaceutical composition comprises 15-25% Ramulus Cinnamomi, 30-40% Radix et Rhizoma Rhei, 15-25% Semen Persicae, 15-25% Radix Rhizoma Glycyrrhiza and 5-10% *Cordyceps*.

11. The-method of claim 10, wherein the pharmaceutical composition comprises 20% Ramulus Cinnamomi, 35% Radix et Rhizoma Rhei, 20% Semen Persicae, 20% Radix Rhizoma Glycyrrhiza and 5% *Cordyceps*.

12. The method of claim 10, wherein the pharmaceutical composition improves insulin sensitivity.

13. The method of claim 10, wherein the pharmaceutical composition increases the binding of insulin and its receptor.

14. The method of claim 10, wherein the pharmaceutical composition increases the absorption of glucose in skeleton muscle and adipocyte so as to effectively decrease the blood sugar level.

15. The method of claim 10, wherein the diabetes is type II diabetes.

16. The method of claim 10, wherein the pharmaceutical composition is orally administered.

* * * * *